United States Patent [19]

McMannis et al.

[11] Patent Number: 5,316,540
[45] Date of Patent: May 31, 1994

[54] APPARATUS AND METHOD FOR SEPARATING MICROSCOPIC UNITS IN A SUBSTANTIALLY CONTINUOUS DENSITY GRADIENT SOLUTION

[75] Inventors: John D. McMannis, Evergreen, Colo.; Nicholas London, Evington, United Kingdom

[73] Assignee: Cobe Laboratories, Lakewood, Colo.

[21] Appl. No.: 3,559

[22] Filed: Jan. 13, 1993

[51] Int. Cl.$^5$ .......................................... B04B 11/00
[52] U.S. Cl. .................................... 494/37; 494/35; 494/45
[58] Field of Search ................... 494/37, 45, 22, 23, 494/27, 28, 31, 35; 422/72; 604/4, 5, 6; 210/781, 782

[56] References Cited

U.S. PATENT DOCUMENTS

| | | | |
|---|---|---|---|
| 3,737,096 | 6/1973 | Jones | 494/37 |
| 4,416,654 | 11/1983 | Hansen | 494/37 |
| 4,806,252 | 2/1989 | Brown | 494/37 |
| 4,850,995 | 7/1989 | Tie | 604/6 |
| 5,114,396 | 5/1992 | Unger | 422/72 |

OTHER PUBLICATIONS

London et al., Chapter 11 on "Islet Purification", Pancreatic Islet Cell Transplantation (1992), pp. 113–123.
English et al., "Semiautomated Processing of Bone Marrow Grafts for Transplantation", Reprinted from Transfusion, Jan. 1989, vol. 29, No. 1, pp. 12–16.
Gilmore et al., "A Technique for Rapid Isolation of Bone Marrow Mononuclear Cells Using Ficollmetrizoate and the IBM 2991 Blood Cell Processor", British Journal of Haematology, 1982, 50, 619–626.
Beaujean et al., "Separation of Large Quantities of Mononuclear Cells from Human Blood Using a Blood Processor", Reprinted from Transfusion, Mar.–Apr. 1985, vol. 25, No. 2, pp. 152–154.
Maniatis et al. Article Entitled "Purification of Closed Circular DNA by Centrifugation to Equilibrium in Cesium Chloride-Ethidium Bromide Gradients", Molecular Cloning, a Laboratory Manual, pp. 93–94 (1982).
"Gradient Makers: Large Volume Gradient Maker-s-SG Series", Hoefer Scientific Instruments Catalog/Brochure (Unknown Publication Date).
Lake et al., "Large-Scale Purification of Human Islets Utilizing Discontinuous Albumin Gradient on IBM 2991 Cell Separator", Diabetes, vol. 38, Suppl. 1, Jan. 1989.
McMannis, Chapter 7 Entitled "Use of the Cobe 2991 Cell Processor for Bone Marrow Processing", Bone Marrow Processing and Purging, A Practical Guide, pp. 73–85 (1991).
Zucker et al., "Canine Islet Purification on Albumin Gradients Using the Cobe 2991 Centrifuge", Cobe Laboratories, Inc., Presented at 2nd International Congress on Pancreatic and Isle Transplantation, Minneapolis, MN., 1989.
"Cobe Protocol for Processing Bone Marrow Using a Density Gradient Separation Medium on the Cobe 2991 Cell Processor" (Nov. 1991).
"2991 Blood Cell Processor-Blood: 'A Drug for Human Use'", Cobe Catalog/Brochure (1989).

*Primary Examiner*—Robert W. Jenkins
*Attorney, Agent, or Firm*—Sheridan, Ross & McIntosh

[57] ABSTRACT

An apparatus and method for the separation of a predetermined type of microscopic unit (e.g., islets of Langerhans) from a given medium (e.g., pancreatic digest) by centrifuging in a substantially continuous density gradient. In one embodiment, a substantially continuous density gradient solution is provided to a flexible processing bag appropriately positioned within an upper chamber of a rotating variable volume centrifuge. The solution having a plurality of the desired microscopic units therein is loaded onto the gradient and such units migrate to a particular radial position within the gradient based upon the density of such units. Once appropriately separated by the formation of regions, a fluid is provided to a lower chamber of the centrifuge bowl during continued rotation thereof to sequentially remove fractions from the processing bag from an inward location to an outward location, at least one of which fractions includes the band of the desired microscopic units. The desired microscopic units of a given fraction(s) may therefore be provided to an appropriate collector.

16 Claims, 7 Drawing Sheets

APPARATUS AND METHOD FOR SEPARATING MICROSCOPIC UNITS IN A SUBSTANTIALLY CONTINUOUS DENSITY GRADIENT SOLUTION

FIELD OF THE INVENTION

The present invention generally relates to the separation of microscopic units (e.g., particular types of cells/cell clusters) from a fluid medium and, in particular, to the separation of such microscopic units by centrifugation in a substantially continuous density gradient solution.

BACKGROUND OF THE INVENTION

Centrifugation utilizes the principle that constituents (e.g., cells, cell clusters) within a medium (e.g., liquid solutions/mixtures) will assume a particular radial position within the centrifuge bowl based upon their respective densities and will therefore separate when the centrifuge is rotated at an appropriate angular velocity for an appropriate period of time. As can be appreciated, there are a variety of centrifuges having features which potentially enhance and/or restrict their use for particular applications. For instance, the COBE 2991 TM Cell Processor is a variable volume centrifuge which is commercially available from the assignee of this patent application and is the subject of U.S. Pat. No. 3,737,096 to Jones et al., issued Jun. 5, 1973. This variable volume centrifuge has a variety of desirable features, including providing a centrifugation system which enhances the potential for maintaining a desired degree of sterility in various of the aspects involved in/relating to the actual separation of such constituents from the medium, such as during the provision of the medium to the centrifuge bowl and during the removal of the separated constituents from the centrifuge bowl.

Generally, a variable volume centrifuge has a substantially flexible diaphragm which separates the centrifuge bowl into upper and lower chambers. A substantially flexible processing bag is positionable within the upper chamber and is used to contain the medium to be centrifuged therein, as well as other appropriate additives. This processing bag is interconnectable with a plurality of sources and collectors via tubing and a centrally located rotating seal. The lower chamber of the centrifuge bowl is used to vary the volume of the upper chamber, and thus the processing bag, to allow for the on-line, sequential harvesting of fractions (i.e., a certain volume of medium) from the processing bag.

In preparation for centrifuging, the processing bag is positioned within the upper chamber of the centrifuge bowl and is interconnected via the rotating seal and tubing to the sources and collectors. The medium to be centrifuged is typically provided to the processing bag after the bag is positioned within the centrifuge bowl. The potential for maintaining a desired degree of sterility is enhanced by providing such medium from at least one of the sources to the processing bag via the tubing (i.e., no additional exposure of the medium is required when providing such to the processing bag). When rotation of the centrifuge is thereafter initiated, the various constituents begin to assume a particular radial position within the centrifuge bowl based upon their respective densities. When appropriate separation has been achieved, a hydraulic or other appropriate fluid is provided to the lower chamber of the centrifuge bowl during continued rotation of the bowl to raise the diaphragm and thus reduce the volume of the upper chamber and the flexible processing bag contained therein. As a result, fractions are sequentially removed from the processing bag via the rotating seal and tubing by order of increasing density and at least one of such fractions will have the desired separated constituents therein. These various fractions may be directed to one or more of the collectors, either for storage and subsequent use and/or for disposition as waste.

Swinging bucket-type centrifuges are also commercially available, one of which is the Mistral 300I by MSE. Generally, the material to be centrifuged is placed in a centrifuge tube having a closable top and is thereafter secured to a radially-extending arm within the centrifuge. A plurality of these radially-extending arms may be utilized by a given centrifuge (typically ranging from a 2 tube capacity to a 25 tube capacity) to increase processing capabilities since the tubes are of generally small volume (e.g., 50 milliliters). Once the centrifuge tubes are appropriately positioned, the centrifuge is rotated such that the arms with the tubes attached thereto swing out to a position determined by centrifugal force. Usually, the tubes assume a substantially horizontal position. Upon rotation of the centrifuge at an appropriate angular velocity and for an appropriate period of time, separation is achieved within each tube based upon the density of the various constituents. Thereafter, the rotation of the centrifuge is terminated, typically by allowing for a free spinning of the centrifuge to the static state to attempt to reduce the potential for disturbing the achieved degree of separation to an undesirable degree. Moreover, this also allows the tubes to return to their initial position. Once rotation of the centrifuge has stopped, the centrifuge tubes are removed therefrom and the desired separated constituents are harvested from the tube, typically by passing a syringe through the top of the tube to withdraw fractions therefrom until the desired separated constituents are removed and collected.

One particular application suited for use of the above-described principles of centrifugation is the harvesting of various types of cells and/or cellular structures from cell mixtures, such as islets of Langerhans from a preparation of a pancreatic digest having such islets and exocrine tissues therein. These harvested islets are useful in the treatment of diabetes by transplantation of the islets or otherwise. In this case it is highly desirable for the centrifugation to produce a high degree of separation, and thus highly-purified islets. For instance, possible advantages associated with transplanting highly-purified islets include increased safety (e.g., reduced health risks), improved islet implantation, and reduced immunogenicity of the graft. N. London, R. James, & P. Bell, "Islet Purification" in Pancreatic Islet Cell Transplantation, Camillo Ricordi, ed. 113 (1992).

One available alternative for the separation of islets from a preparation of a pancreatic digest is by utilizing centrifugation in which, generally, separation is primarily based upon cell density. One type of such centrifugation is centrifugation in a discontinuous density gradient, and these gradients have been utilized in the harvesting of islets both in variable volume centrifuges and swinging bucket type centrifuges of the above-described types.

Figure 1:
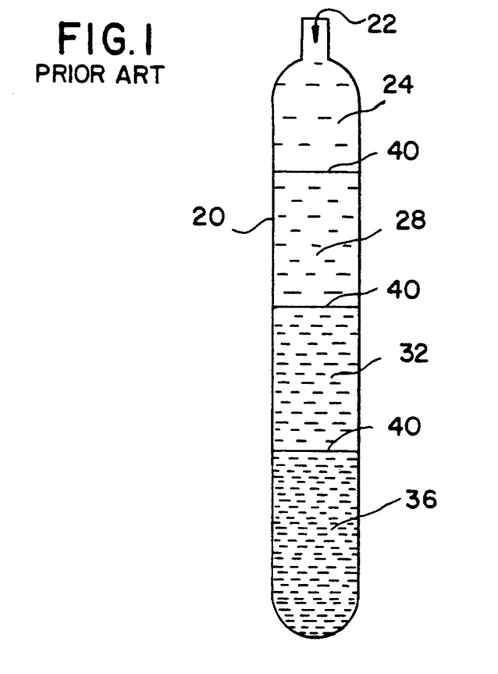
FIG. 1 illustrates a prior art separation technique utilizing a centrifuge tube and a discontinuous density gradient.

Separation by centrifugation utilizing a discontinuous density gradient will be explained herein by reference to a swinging bucket type centrifuge and generally entails the use of a plurality of solutions having known but differing densities such that a pre-established, vertically layered configuration is metered into a tube 20 as illustrated in FIG. 1. In this case, a discontinuous density gradient 22 is formed by first, second, third, and fourth solutions 24, 28, 32, 36 which have different densities, the densities of the various solution layers increasing in moving down the gradient 22 as indicated by the spacing changes in the solution designations (i.e., the density of the first solution 24 is less than the density of the second solution 28 and so forth). By selecting appropriate density solutions for the gradient 22, the desired cell(s) to be harvested will collect at least at one of the three interfaces 40, or at the top or bottom of the tube 20, during rotation of the centrifuge (swinging bucket type) in which the tube 20 is positioned in the above-described manner, whereas remaining portions of the cell mixture will collect at other interfaces 40 within the gradient 22. Therefore, the desired cells will separate from remaining portions of the cell mixture during centrifugation and can be harvested by removing the tube 20 from the centrifuge and drawing the desired cells off in a syringe in the above-described manner.

As noted above, instead of having the discontinuous density gradient 22 within the tube 20, in the case where a variable volume centrifuge of the above-described type is utilized the gradient 22 may be provided to its flexible processing bag and be radially extending therein. This again allows for on-line, sequential removal of fractions to obtain the desired cells which collect at one or more of the interfaces 40 which would be substantially annular and positioned at varying radial distances from the rotational axis of the centrifuge bowl.

Cell separation by utilizing a discontinuous density gradient has a number of disadvantages. For instance, the operative part of the gradient is the zone at each interface 40 within the gradient 22. More particularly, the various solution densities are selected such that the desired cell will pass through, for instance, the first and second solutions 24, 28 (i.e., the cells will have a greater density than each of these solutions), but will have a density which is less than that of the third solution 32 such that the cells will collect at the interface 40 between the second and third solutions 28, 32. Furthermore, the other constituent(s) of the mixture containing such cells will, on the other hand, have for instance a density such that these constituents will pass through the first, second, and third solutions 24, 28, 32, but will have a density less than that of the fourth solution 36 such that these constituents will collect at the interface 40 between the third and fourth solutions 32, 36. Based upon this separation technique, it can be appreciated that the interfaces 40 may become occupied by cells during centrifugation to the degree where such cells will act as a barrier to the movement of other constituents within the cell mixture toward a more radially outwardly positioned interface 40, particularly in the case where the material to be centrifuged is "top loaded" onto the gradient 22. "Top loading" is where the material to be centrifuged is provided to the tube 20 after the gradient 22 is in the tube 20. Consequently, this effectively limits the amount of cell mixture which may be processed utilizing a discontinuous density gradient.

Related to the foregoing clogging problem at the interfaces 40 often associated with discontinuous density gradients 22 is that an overloading of the gradient 22 may introduce a certain instability to the gradient 22 which may adversely affect separation. Moreover, in the event that the cells and other constituents of the cell mixture have relatively close densities, the potential increases for such clogging at the interfaces 40 of a particular density, and thus may result in a reduction in the purity of the cells to be harvested. Moreover, in order to enhance the effectiveness of the separation by a discontinuous density gradient 22, the individual gradient layers should preferably be selected based upon certain criteria since the characteristics of the cells and/or cell mixture may vary depending upon, for instance, the donor/source and/or the manner in which the cell mixture is obtained. Further, the characteristics of the cells obtained from a given donor or source may vary.

Figure 2:
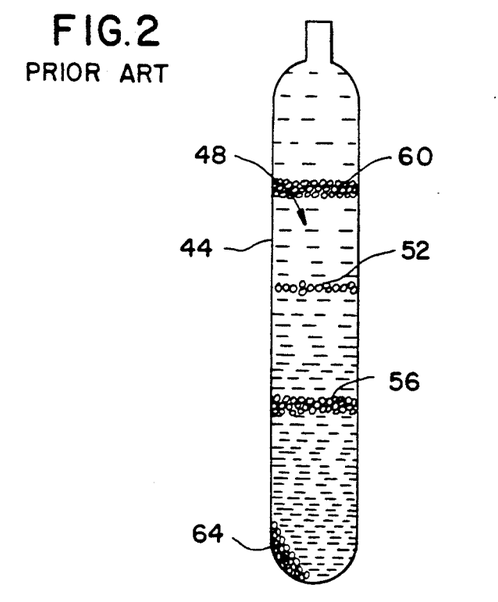
FIG. 2 illustrates a prior art DNA/RNA separation technique utilizing a centrifuge tube and a continuous density gradient.

Another type of gradient which may be utilized in separation by centrifugation is a continuous density gradient in which the density changes continuously throughout the gradient solution (e.g., there are infinitesimal interfaces) such that the cells effectively migrate to their respective buoyant densities within the gradient solution. This has been utilized in the above-described types of swinging bucket centrifuges having the substantially rigid wall centrifuge tubes for containing the gradient solution and the material to be separated by centrifuging. One particular application in which a continuous gradient has been utilized is in the separation of DNA and RNA molecules as illustrated in FIG. 2. In this case, a gradient solution (not yet established) is provided to the tube 44, as well as the solution containing the DNA/RNA molecules. In this particular application, the limited volumetric capacity of the tube 44 is tolerable since the amount of DNA and RNA molecules which may be collected in this tube 44 is sufficient for the intended uses of such molecules.

The continuous gradient 48 is established within the tube 44 by rotating the swinging bucket-type centrifuge at a sufficiently high velocity and for an extended period of time such that the gradient 48 is established within the tube 44 (e.g., 45,000 RPM for 36 hours). As a result, the DNA and RNA molecules each migrate to their respective positions within the gradient solution based upon their particular densities. In this regard, the DNA molecules collect at first and second regions 52, 56, whereas other portions of the mixture such as the protein migrate further within the gradient solution to form a third region 60. The RNA may actually pass completely through the gradient 48 as illustrated by a pellet 64.

A continuous gradient of the above-described type has also been utilized in the selection of the particular gradient solution layers (e.g., solution densities) to be used in a discontinuous density gradient separation method utilizing a variable volume centrifuge since as noted above it is desirable to adapt each gradient to certain characteristics. Moreover, a continuous gradient has been used in a centrifuge in which the centrifuge tube is maintained in a substantially vertical position such that the gradient is radially established therewithin (i.e., horizontally extending). When appropriate separation has been achieved in this particular case, the centrifuge tube is removed from the centrifuge and the gradient actually inverts such that it extends vertically within the centrifuge tube. The desired fraction(s) may thereafter be harvested from the centrifuge tube in the above-described manner.

SUMMARY OF THE INVENTION

The present invention is an apparatus and method for separating a plurality of a predetermined type of microscopic unit from a fluid medium containing such microscopic units. As used herein, the term "microscopic unit" includes, but is not limited to, cells and cell clusters that may or may not be visible to the naked eye. More particularly, the present invention utilizes the principles of centrifugation and the use of a substantially continuous density gradient solution to allow for the separation of such microscopic units.

In one aspect of the present invention, the above-described separation of the plurality of microscopic units is provided by utilizing a rotatable centrifuge and a processing container which is positionable within the centrifuge and rotatable therewith. The container holds the microscopic unit-containing fluid as well as the substantially continuous density gradient solution during centrifugation. In order to reduce the time period required to establish the gradient, and thus the potential for damage to the plurality of microscopic units, and to thereafter enhance the maintenance of the linearity of the gradient, the continuously varying gradient solution is established externally of the centrifuge and the gradient solution is dispensed into the container during rotation of the centrifuge. The microscopic unit-containing fluid may be provided to the container before the introduction of the gradient solution thereto (i.e., bottom loading), or alternatively is provided after the gradient solution is in the container (i.e., top loading), such as in the case where the microscopic units are islets of Langerhans and the fluid is a preparation of a pancreatic digest.

During the rotation of the centrifuge, the plurality of microscopic units assume a position within the gradient solution based upon a density of such units and thus become separated from remaining portions of the fluid having different densities. More particularly, each of the microscopic units migrates to that portion of the gradient solution which has substantially the same density as such unit. Since all of microscopic units may not necessarily have exactly the same density, there may be one or more regions of separated microscopic units within the container. Moreover, within each of these regions there may be some type of probabilistic distribution of the microscopic units based upon their individual densities.

Once a desired degree of separation has been achieved in accordance with the above-identified aspect, the present invention may also provide for the removal of the microscopic units within one or more of the regions from the container. A number of features may be incorporated relating to this removal in an attempt to maintain the degree of separation achieved during centrifugation. For instance, removal may be performed during continued rotation of the centrifuge. This also effectively provides a closed system which enhances the potential for maintaining a desired degree of sterility associated with the entire procedure since materials can thus be both provided to and removed from the centrifuge during rotation via, for instance, a tubing harness connected to one or more fluid sources (e.g., a preparation of a pancreatic digest) and collection containers (i.e., for the islets of Langerhans harvested from the digest pursuant to the present invention). Moreover, the general orientation of the gradient solution and the container may be maintained during removal of the microscopic units similar to the orientation of the gradient solution and container assumed during centrifugation to further assist in maintaining the degree of separation provided by centrifugation (e.g., substantially horizontal). Consequently, the potential is reduced for disturbing the gradient to the degree where the separation achieved is adversely affected.

In another aspect of the present invention, the described separation of the microscopic units utilizes a centrifuge having a rotational axis and a processing container. The container is positionable within the centrifuge and contains the microscopic unit-containing fluid and the substantially continuous density gradient solution during centrifugation. With further regard to the container, it has upper and lower portions which extend radially relative to the rotational axis of the centrifuge. During rotation of the centrifuge, the gradient also extends radially within the container relative to the rotational axis and the plurality of microscopic units thereby assume a radial position therewithin based upon the density of the units in the above-described manner. After an appropriate period of time for centrifugation, the plurality of microscopic units sufficiently separate from remaining portions of the microscopic unit-containing fluid into the above-noted one or more regions and may be thereafter removed from the container. In this regard, the microscopic units in this aspect are removed while the upper and lower portions of the container remain in substantially its full radial extent. Therefore, the potential is reduced for a disturbance of the gradient which may adversely affect the purity of the separated microscopic units.

Although there may be a number of ways to remove the microscopic units from the container while maintaining the described orientation of the container and the gradient as noted above, such may be provided by utilizing a substantially flexible container. Consequently, an appropriate force may be exerted upon the container when removal is desired to force contents out of the container, namely by changing the profile, and thus the volume, of the container. In addition, this allows for such removal to be performed while continuing the rotation of the centrifuge which further enhances the maintenance of the separation.

In another aspect of the present invention, the above-described separation of the plurality of microscopic units utilizes a centrifuge and a processing container for retaining the microscopic unit-containing fluid and substantially continuous density gradient solution during centrifugation. The container is formed from a substantially flexible material such that the profile of the container during centrifugation is thus determined at least in part by the volume of the gradient solution and microscopic unit-containing fluid contained therein. Moreover, the plurality of microscopic units assume positions within the gradient solution as noted above based upon the densities of such units, and are thereby separated during centrifugation from remaining portions of the microscopic unit-containing fluid having different densities. Upon achieving a desired degree of separation, such units may be removed from the container by changing the profile of the container, which is again possible due to its flexibility.

The described modification of the profile of the container to achieve removal in one embodiment may be provided by positioning a substantially flexible diaphragm in the centrifuge to create upper and lower chambers. In this case, the flexible container is positioned within the upper chamber such that when removal of materials therefrom is desired, an appropriate fluid may be provided to the lower chamber to raise the diaphragm. This exerts a force on the container which changes its profile and thus forces the materials out therefrom. Desirably, this may be done in a manner such that the gradient solution is not disturbed and such that removal of materials from the processing bag is done sequentially, such as by order of increasing density.

In another aspect of the present invention, the above-described separation of the plurality of microscopic units utilizes a centrifuge having a rotational axis and a container which is positionable within the centrifuge and which functions at least in part to retain the microscopic unit-containing fluid and the substantially continuous density gradient solution during centrifugation. When the centrifuge is rotated about its rotational axis, the microscopic units migrate to positions within the gradient solution based upon the densities of such units. As noted above, all of such units may not necessarily have the same density such that there may be one or more regions of microscopic units each having a given distribution. As can be appreciated, it may be desirable to maximize the area of this boundary region since this maximizes the amount of microscopic units of a particular density which may be collected without increasing the potential for introducing impurities into the separation (e.g., units of similar densities may begin moving into a lighter density portion of the gradient solution if this boundary region area is too small, thereby potentially increasing the lateral extent of the region containing such units if too much of the medium is processed), and without increasing the size of the centrifuge to an undesirable degree. Once separated in this manner, the microscopic units may be removed from the container.

In another aspect of the present invention, the above-described separation utilizes a centrifuge and a processing container which is positionable within the centrifuge and which contains the microscopic unit-containing fluid and substantially continuous density gradient solution during centrifugation. When the centrifuge is rotated, the plurality of microscopic units separate from remaining portions of the fluid within the gradient solution based upon a density of the units in the above-described manner. Once a desired degree of separation has been achieved, the plurality of separated microscopic units may be harvested from the container while the centrifuge continues to rotate, thereby allowing for on-line removal of the units. As can be appreciated, this may allow for a harvesting of the units while maintaining the orientation of the gradient solution, which substantially maintains the purity of the separation achieved during centrifugation.

One embodiment which incorporates each of the above-identified aspects of the present invention utilizes a variable volume centrifuge for the separation of the plurality of microscopic units within the substantially continuous density gradient solution. The variable volume centrifuge includes a centrifuge bowl having a base portion and an outer rim. The centrifuge bowl is separated into upper and lower chambers by a substantially flexible diaphragm which is attached to inner and outer portions of the base. A substantially flexible processing container is positionable within the upper chamber and may be appropriately secured to a rotating portion of the centrifuge bowl. This container is fluidly connected via a rotating seal and appropriate tubing to one or more sources (e.g., for the microscopic unit-containing fluid, for the substantially continuous density gradient solution) and/or collection containers (e.g., for receiving the harvested plurality of microscopic units). Moreover, the container is substantially annular relative to the rotational axis of the centrifuge with a radial extent when positioned in the centrifuge bowl.

When the processing container is positioned within the centrifuge bowl and appropriately secured thereto to allow for simultaneous rotation, the gradient solution may be provided to the container via the rotating seal and tubing during rotation of the centrifuge. This not only reduces the time period required to establish the gradient (e.g., extended periods of time may be required to establish a substantially continuous density gradient from a solution strictly through centrifugation, such that if the microscopic units are contained therein during this extended centrifugation, the potential for damage to the units may undesirably increase), but enhances the maintenance of the linearity of the gradient within the container as well. With the gradient solution being within the container, the microscopic unit-containing fluid is provided to the rotating container in a low density solution (i.e., top loading), although bottom loading may be possible (i.e., introducing the units to the container in a high-density solution prior to provision of the gradient solution to the container).

As can be appreciated, due to its flexibility the profile of the container is defined at least in part by the volume of qradient solution therein. Consequently, the amount of gradient solution provided to the container and the density range thereof may be selected to maximize the amount of microscopic units which may be separated with a desired degree of purity. More particularly, the microscopic units will each assume a radial position within the gradient solution based upon the density of such individual units, and the outward radial movement of such units in the gradient solution in the case of the described top loading will be terminated by the density of the adjacent, heavier density portions of the gradient solution. Consequently, in order to have this radial position of at least one of the regions of separated microscopic units coincide with a portion of the centrifuge bowl such that the area of this boundary between such region and an adjacent portion of the gradient is maximized to maximize the number of units of a particular density which may assume this position (e.g., a maximum height of the centrifuge bowl at the maximum radial distance, considering, however, the effects of positioning the plurality of microscopic units in proximity to the centrifuge rim), the gradient density range and/or volume may be appropriately selected.

When a desired degree of separation has been achieved, an appropriate hydraulic fluid may be provided to the lower chamber of the centrifuge bowl during continued rotation of the centrifuge to raise the substantially flexible diaphragm to reduce the volume of the upper chamber and the substantially flexible container positioned therein. This initially causes those fractions nearest the rotational axis of the centrifuge bowl to be removed from the container via the rotating seal connection by a changing of the profile of the container. This is again due to the container's flexibility and the forces exerted thereon by the hydraulic fluid being provided to the lower chamber. When the fraction of the region(s) of microscopic units is removed from the container in this same manner, such may be diverted to an appropriate collection system. As can be appreciated, this on-line harvesting substantially maintains the radial extent of the gradient solution, and thus desirably maintains the achieved degree of separation of the microscopic units.

DETAILED DESCRIPTION

The present invention will be described with reference to the accompanying drawings which assist in illustrating the pertinent features thereof. In this regard, the present invention is generally an apparatus and method for the separation of a predetermined type of microscopic unit (e.g., cells, cell clusters) utilizing the principles of centrifugation and a substantially continuous density gradient solution. Although the principles of the present invention may be utilized in a plurality of applications, in one embodiment such microscopic units are islets of Langerhans which are contained within a preparation of a pancreatic digest.

Each of the various aspects of the present invention involve separation by centrifugation. Although a number of centrifuges may be appropriately incorporated by the present invention, the centrifuge 72 of FIG. 3 has a plurality of features which provide for each of such aspects in a particularly desirable manner. Generally, the centrifuge 72 is referred to as being of a variable volume configuration and one such configuration is disclosed in U.S. Pat. No. 3,737,096 to Jones, et al., issued Jun. 5, 1973, and entitled "BLOOD PROCESSING CONTROL APPARATUS." U.S. Pat. No. 3,737,096 is assigned to the assignee of this patent application and the entire disclosure of such is hereby incorporated by reference herein. Moreover, this particular variable volume centrifuge 72 is commercially available from the assignee of this patent application and is known as the COBE 2991 TM Cell Processor. Notwithstanding the specific reference to this particular type of centrifuge herein, those skilled in the art will appreciate that such is merely an exemplary description of the principles of the present invention.

The principles of the operation of the centrifuge 72 for the separation of the various constituents within a given medium may be applied in whole or in part to each of the above-identified aspects of the present invention. Generally and referring to FIG. 3, the centrifuge 72 incorporates a centrifuge bowl 76 which is defined by a base 80 and a centrifuge rim 92. The bowl 76 is separated into upper and lower chambers 116, 120 by a substantially flexible diaphragm 104 which is appropriately attached to annular interior and exterior portions of the base 80. The upper chamber 116 receives a processing bag 136 for containing the materials to be centrifuged and the lower chamber 120 receives an appropriate fluid (e.g., hydraulic fluid) from a volume variation assembly 276 for purposes of varying the volume of the upper chamber 116 to remove fractions from the processing bag 136 after appropriate separation by centrifugation. In this regard, the processing bag 136 is interconnected to first, second, third, and fourth containers 296, 300, 304, and 308 via a tubing harness 172 and rotating seal 176 such that a medium may be provided to and removed from the processing bag 136 during rotation of the centrifuge bowl 76.

Figure 4:
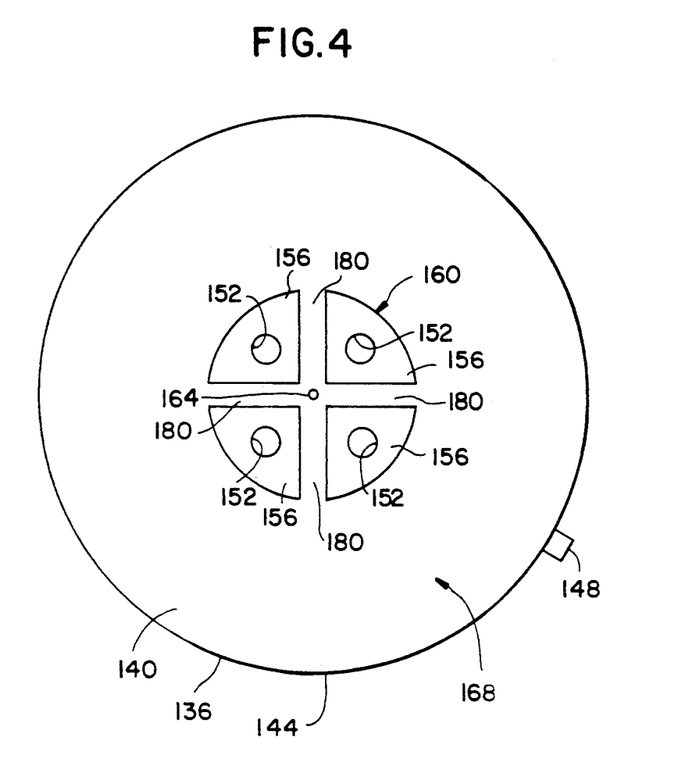
FIG. 4 is one embodiment of a processing bag for use with the centrifuge of FIG. 3.

One embodiment of the processing bag 136 is more particularly illustrated in FIG. 4. The processing bag 136 is formed from a substantially flexible material, such as polyvinyl chloride, and has radially extending upper and lower surfaces 140, 144 which are appropriately secured along the perimeter of the bag 136. Based upon the flexibility of the bag 136, the profile of the bag 136 is determined at least in part by the amount of fluid contained therein (e.g., FIGS. 5A-5D). Moreover, the ability of the bag 136 to change profiles is also utilized at least in part to remove materials therefrom during rotation of the centrifuge bowl 76 as will be discussed below.

The processing bag 136 includes four mounting holes 152 which are sealed from the interior portion of the bag 136 to define four quadrants 156 of an inner portion 160 of the processing bag 136. Each pair of adjacent quadrants 156 defines a radially-extending channel 180 which interconnects the axial entry port 164 to the processing bag 136 to its outer, annular, portion 168. The tubing harness 172 (FIG. 3) is interconnected with the axial entry port 164 to allow for the introduction and removal of fluids from the processing bag 136 during centrifuging. A receptacle 148 is also provided for providing fluid access to the processing bag 136 in the static state, such as when out of the centrifuge bowl 76.

Figure 3:
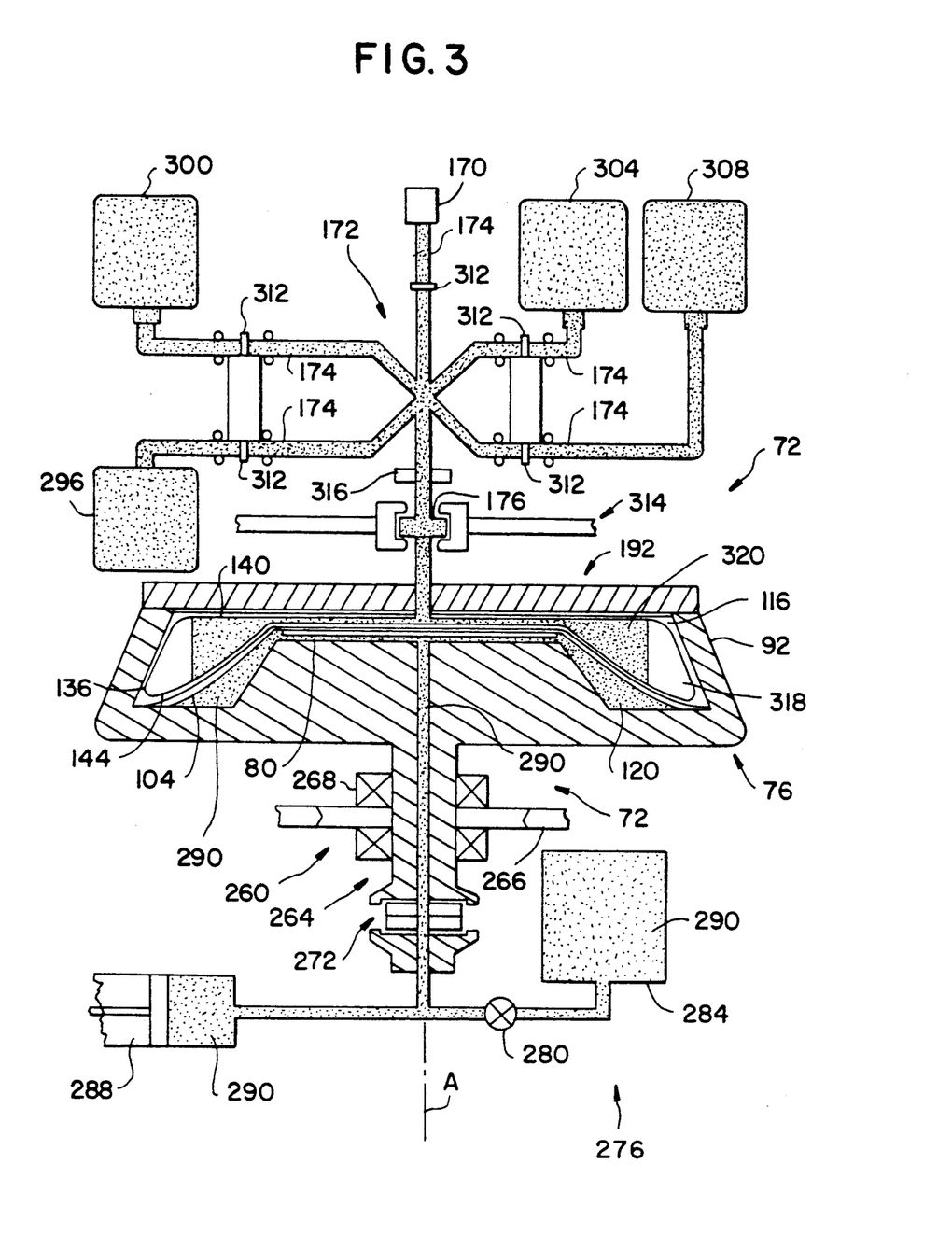
FIG. 3 is a cross-sectional, general schematic representation of one embodiment of a variable volume centrifuge and potential interconnections with fluid sources/collection containers.

When the processing bag 136 is positioned in the upper chamber 116 of the centrifuge bowl 76, a cover assembly 192 is positioned over and secured to the centrifuge bowl 76 in an appropriate manner. Once again, the tubing harness 172 interconnects the first, second, third, and fourth containers 296, 300, 304, 308 with the processing bag 136 via a rotating seal 176, and valves 312 may be appropriately incorporated in each of the lines 174 leading to such containers 296, 300, 304, 308 to control the various flows. A positioning cover 314 (only partially shown) may be engaged so as to retain the rotating seal 176.

The medium to be centrifuged may be contained within the first container 296 and provided to the processing bag 136 after the processing bag 136 is positioned in the centrifuge bowl 76 and initiation of rotation thereof due to the interconnection provided by the rotating seal 176 and tubing harness 172. In this regard, the centrifuge 72 is rotated by a spindle drive assembly 260 which includes a shaft assembly 264 which engages the bottom of the centrifuge bowl 76, a pulley 268 which is attached to the shaft assembly 264, and a belt 266 which is interconnected with an appropriate drive means (not shown). Rotation of the centrifuge bowl 76 by the spindle drive assembly 260 directs the heavier density constituents of the medium within the processing bag 136 toward the centrifuge rim 92 of the centrifuge bowl 76 (e.g., constituents within a first region 318), while those lighter density constituents remain closer to the central portion (e.g., constituents within a second region 320 and illustrated as being partially removed from the processing bag 136). At an appropriate time during centrifuging, a hydraulic fluid 290 may be introduced into the lower chamber 120 through the shaft assembly 264 via the volume variation assembly 276 to, for instance, remove the lighter density separated constituents of the medium, such as constituents within the second region 320, from the centrifuge bowl 76.

With further regard to the volume variation assembly 176, it includes a hydraulic reservoir 284, a hydraulic pump 288, and a valve 280, and is interconnected with the lower chamber 120 of the centrifuge bowl 76 via the shaft assembly 264. Consequently, when it is desirable to remove constituents from the processing bag 136, the valve 280 may be closed and the hydraulic pump 288 may be activated such that hydraulic fluid 290 is provided to the lower chamber 120 to raise the diaphragm 104 and thereby force the lighter density constituents within the second region 320 out of the centrifuge bowl 76 through the tubing harness 172 and into one or more of the second, third, or fourth containers 300, 304, 308. More particularly, the fluid 290 exerts a force on the lower surface 144 of the processing bag 136 and serves to change the profile of such. This change in profile results in the removal or harvesting of fractions from the processing bag 136 from an inward to outward sequence (i.e., fractions are sequentially removed in order of increasing density). In order to monitor the removal of such fractions, a cell detector 316 may be positioned within a portion of the tubing harness 172.

Figure 5A:
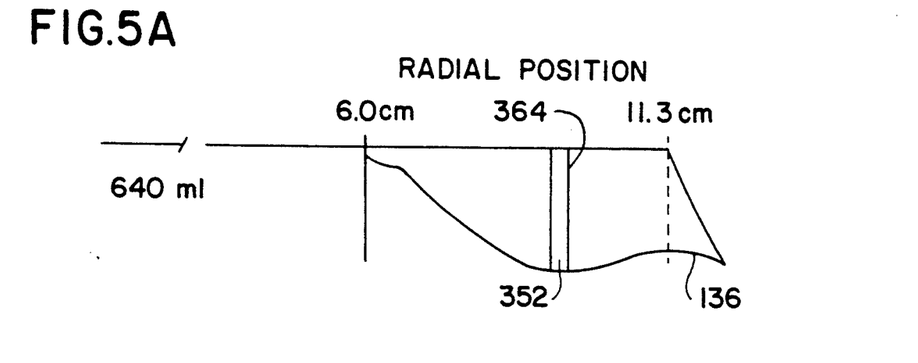
FIGS. 5A-5D are profiles of the processing bag of FIG. 4 with varying amounts of a fluid therein.
Figure 5B:
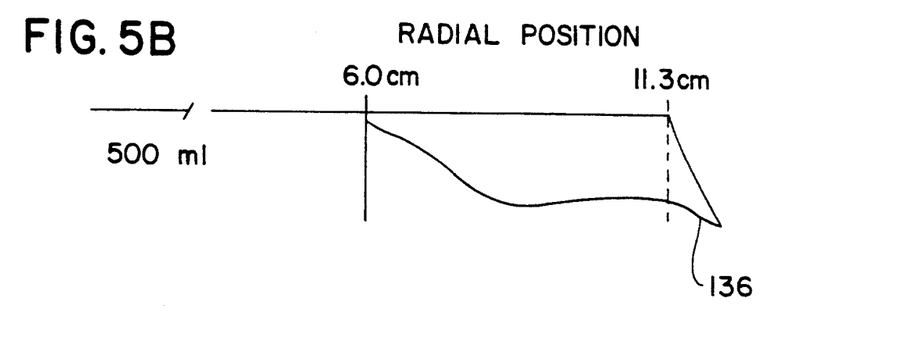
Figure 5C:
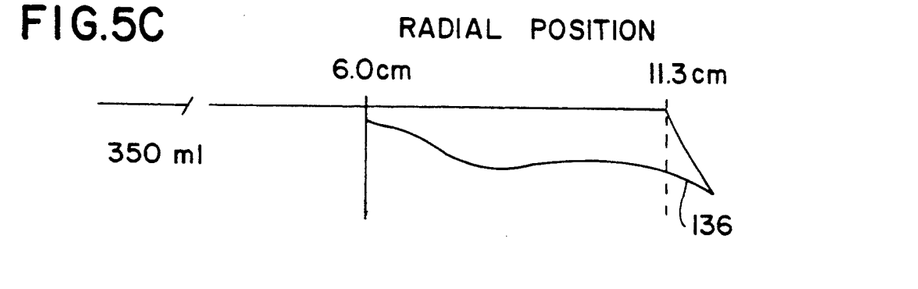
Figure 5D:
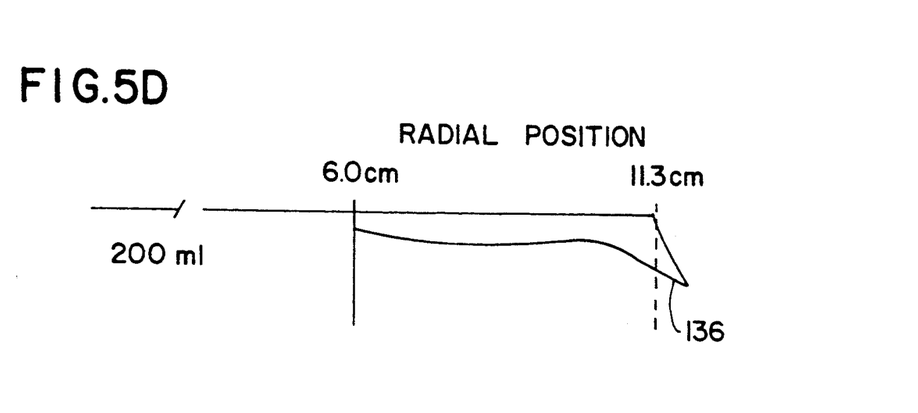

The changes in the profile of the bag 136 during harvesting operations are more particularly illustrated in FIGS. 5A–5D. In FIG. 5A, the processing bag 136 contains 640 ml. of the materials being centrifuged (e.g., any gradient solution and the actual constituent mixture) and such is illustrated from a point 6.0 cm. from the rotational axis A of the centrifuge bowl to a position coinciding with the upper portion of the centrifuge rim 92 which is approximately 11.3 cm. from the rotational axis A. As hydraulic fluid 290 is provided to the lower chamber 120 (FIG. 3) once appropriate separation of the various constituents is achieved, the profile of the bag 136 progressively changes by removal of materials therefrom as a result of the introduction of hydraulic fluid 290 into the lower chamber 120 (FIG. 3) in the above-described manner. This change in profile is illustrated in FIGS. 5B–5D in which the volume of fluid within the processing bag 136 is reduced to 500 ml., 350 ml., and 200 ml., respectively. Although the change in profile of the processing bag 136 has been described with specific regard to the removal of materials therefrom, those skilled in the art will appreciate that the profile of the bag 136 will also be initially determined by the amount of fluid provided thereto. Consequently, the bag 136 may in fact initially have the profile of FIG. 5B if a reduced preparation of material to be centrifuged is provided to the bag 136 in the above-described manner. In this case, the subsequent deformation/changes in profile thereof to achieve removal of various fractions from the bag 136 would be similar to that illustrated in FIGS. 5C–5D.

Continuing to refer to FIG. 3, after the desired constituents have been removed from the centrifuge bowl 76, an additional medium may be again provided to the processing bag 136 for centrifuging. In this case, this medium may be again provided to the centrifuge bowl 76 while the centrifuge bowl 76 continues to spin. With the valve 280 open, the medium provided to the bowl 76 will force, through the diaphragm 104, the hydraulic fluid 290 from the lower chamber 120 to the hydraulic reservoir 284. In the event that no additional centrifuging is to take place, the centrifuge 72 is stopped and the valve 280 is opened such that the hydraulic fluid 290 flows from the lower chamber 120 to the hydraulic reservoir 284. This also lowers the diaphragm 104 by gravity.

Based upon the foregoing, it can be appreciated that the variable volume centrifuge 72 has a plurality of features which are suited to the harvesting of islets of Langerhans from a substantially continuous density gradient solution in accordance with each of the aspects of the present invention. For instance, the variable volume centrifuge 72 provides a closed system in that materials can be provided to and removed from the processing bag 136 without significant exposure of the materials to environmental conditions. Consequently, sterility is desirably maintained. Moreover, the size of the processing bag 136 (e.g., 650 ml. capacity) allows for increased processing capabilities of preparations of pancreatic digest over, for instance, swinging-bucket type centrifuges which utilize fix-walled centrifuge tubes of relatively small volumetric capacity.

The on-line harvesting capabilities of the centrifuge 72 also increases the potential for isolating and collecting islets of a desired purity since the gradient solution is not substantially disturbed during such collecting. More particularly, the orientation of the processing bag 136 and of the contents therein (e.g., being generally radially extending) is not significantly modified in the transformation from separation to harvesting of the various constituents. Moreover, vortexing throughout the gradient solution is reduced or eliminated since the centrifuge 72 does not have to be decelerated or stopped for removal of the various fractions therefrom, at least one of which will contain islets. The variable volume centrifuge 72, particularly its ability to receive a medium during rotation, also allows for establishing the gradient externally of the centrifuge 72 and providing the gradient solution to the processing bag 136 during rotation of the bowl 76, thereby reducing the time for establishing the gradient. Consequently, the exposure time of the islets to centrifuging and the effects, if any, of the gradient solution on the islets is reduced which enhances the maintenance of their condition.

Figure 6:
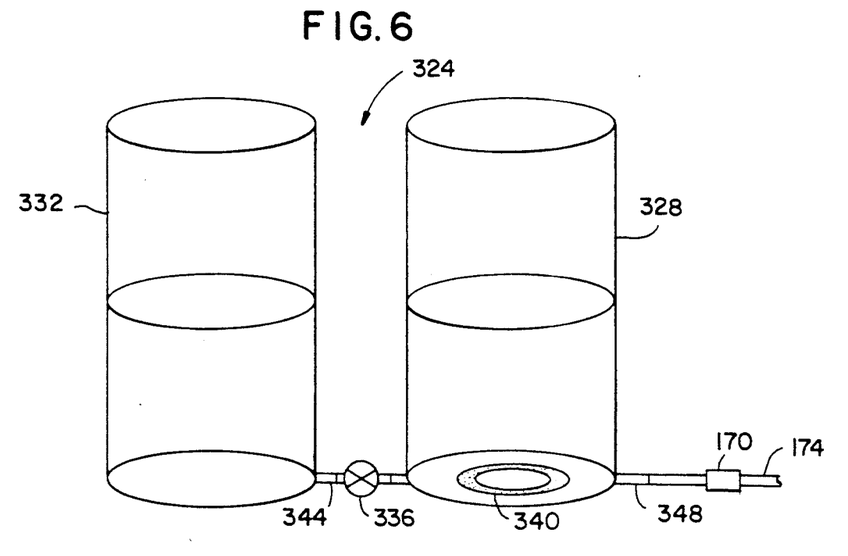
FIG. 6 is a general schematic representation of one embodiment of a substantially continuous density gradient maker.

As noted, the substantially continuous density gradient solution may be provided to the processing bag 136 through the tubing harness 172 during rotation of the centrifuge bowl 76. Although a variety of methods may be utilized for establishing this substantially continuous gradient, one apparatus which may directly provide the substantially continuous gradient solution to the processing bag 136 is illustrated in FIG. 6. One such gradient maker is the Hoefer SG500 and is commercially available from Hoefer Scientific Instruments of 654 Minnesota St., San Francisco, Calif. 94107.

The gradient maker 324 is only generally depicted and includes first and second containers 328, 332 which are appropriately interconnected by tubing 344. The first container 328 contains a high density solution (e.g., 1.09 s.g.) and the second container 332 contains a low density solution (e.g., 1.06 s.g.). The high density and low density solutions are infinitely miscible with each other. The first container 328 may be appropriately interconnected with one tube 174 (FIG. 3) of the tubing harness 172 by tubing 348 and an adapter 170 such that the gradient solution may be directly provided to the processing bag 136 (FIG. 3) during rotation thereof. In this regard, in order to set up the substantially continuous gradient in an effective manner, rotation of the centrifuge 72 is initiated and the high density solution from the first container 328 is allowed to begin flowing into the processing bag 136 (FIG. 3). When an appropriate amount has been provided to the processing bag 136 (FIG. 3), the valve 336 between the first and second containers 328, 332 is opened by a predetermined amount such that the high density solution in the first container 328 becomes continually diluted at an appropriate rate such that the continuous gradient is set up within the processing bag 136 (FIG. 3). In order to enhance the continuity of the gradient, a magnetic stirrer 340 may be incorporated into the bottom portion of the first container 328.

Figure 7:
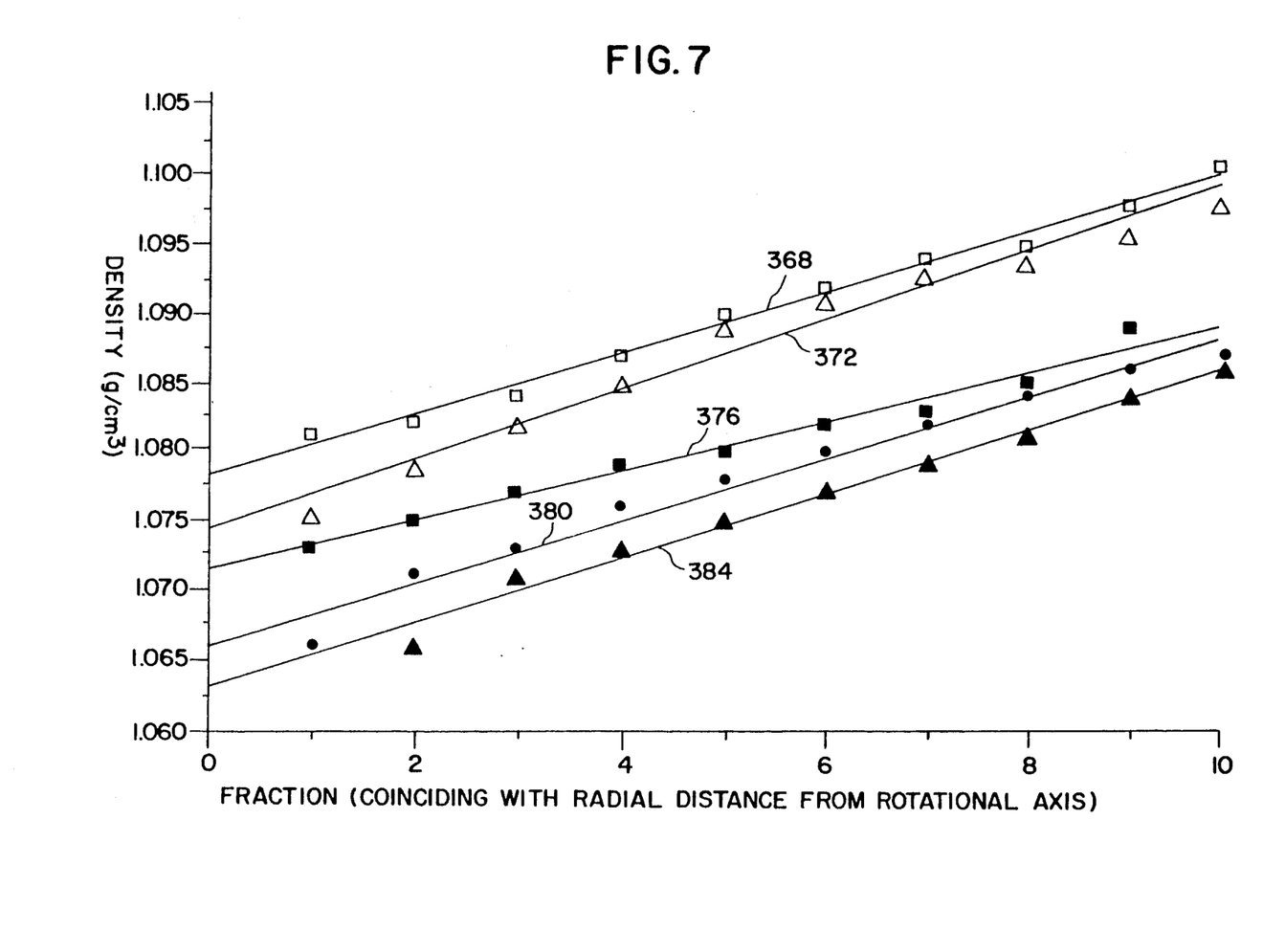
FIG. 7 is a graph illustrating the density changes through five separate substantially continuous density gradients provided to the centrifuge of FIG. 3.

The linearity of the substantially continuous density gradients within the flexible processing bag 136 when positioned within the centrifuge bowl 76 and during rotation thereof is illustrated by the data presented in FIG. 7 from actual testing. Five separate gradients were set up within the processing bag 136 (FIG. 3) in the above-described manner utilizing varying ranges of densities to determine the effect, if any, such density range would have on linearity of the gradient. In this regard, substantially linearity was achieved in each of the gradients as noted by the table below.

| Gradient Ref. No. | Variance |
| --- | --- |
| 368 | 0.992 |
| 372 | 0.980 |
| 376 | 0.985 |
| 380 | 0.978 |
| 384 | 0.971 |

Once the substantially continuous density gradient solution is contained within the processing bag 136, the islets may be loaded onto the gradient solution. In this regard, the preparation of the pancreatic digest containing the islets and exocrine is introduced into the rotating processing bag 13 through the tubing harness 172 in a low density solution, such as one having a density substantially equal to that contained within the second container 332 of the gradient maker 324. Once within the processing bag 136, the islets migrate within the gradient solution (radially outward) to a position within the gradient solution having the same or similar density.

Figure 8:
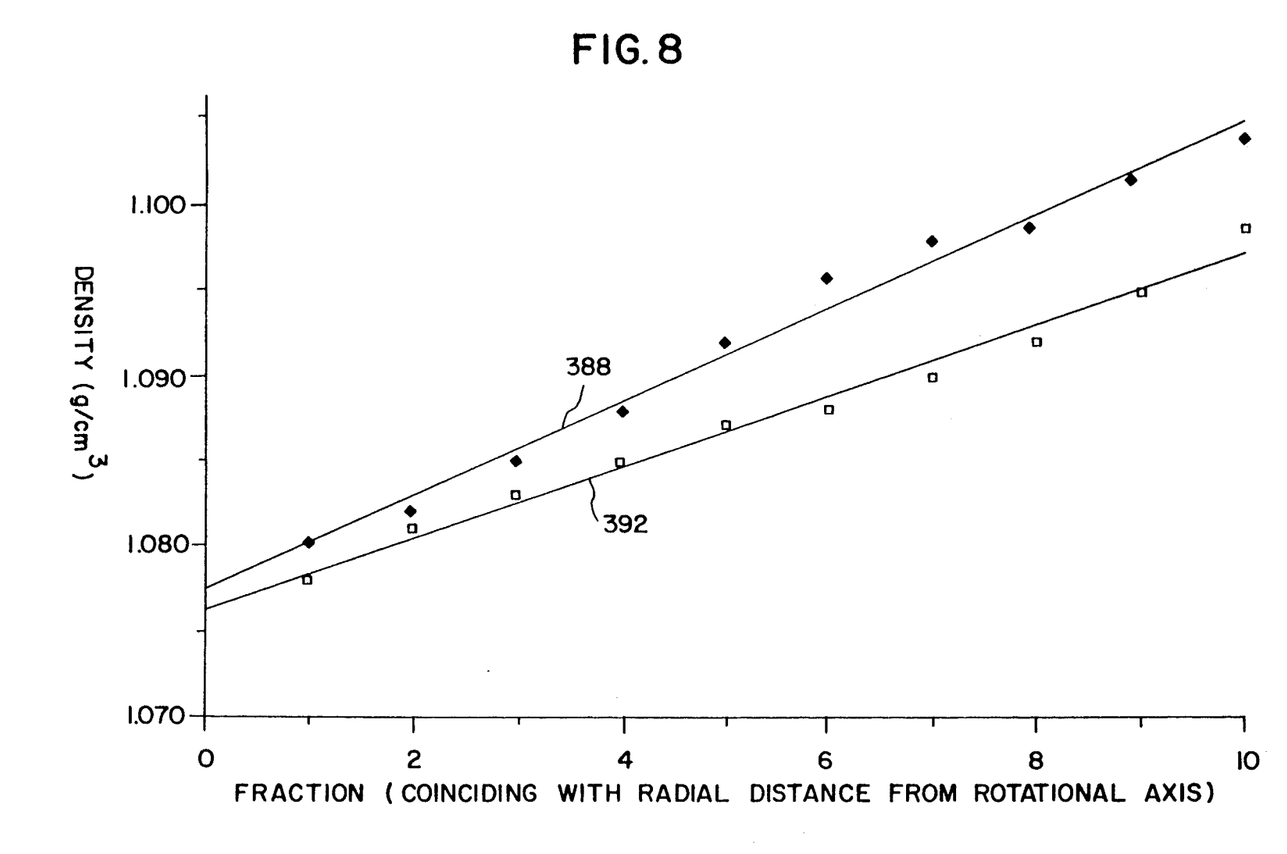
FIG. 8 is a graph illustrating two substantially continuous density gradients provided to the centrifuge of FIG. 3 after top loading a preparation of pancreatic digest thereon.

The described manner in which the islets are provided to the gradient solution within the bag 13 is referred to as top loading since the islets are initially provided to the lowest density portion of the gradient solution and travel radially outward therein to a position coinciding with their density. This manner of loading the islets does not significantly adversely affect the linearity of the gradient as illustrated in FIG. 8. In FIG. 8, data is presented on two separate loadings of islets within 40 ml. of a pancreatic digest onto established gradients. After loading, the variance of the first gradient 388 was 0.986, whereas the variance for the second gradient 392 was 0.928.

Although the present invention has been described with regard to top loading of the pancreatic digest onto the gradient solution, it may be possible to bottom load and achieve a desirable degree of separation. In this case, the pancreatic digest would be provided to the processing bag 136 in a high density solution prior to the introduction of the gradient solution to the processing bag 136. Once the gradient solution is provided to the processing bag 136 in the above-described manner, the islets will migrate radially inwardly to a position coinciding with their buoyant density. Consequently, this manner of loading may also provide for an acceptable degree of separation of islets.

Figure 9:
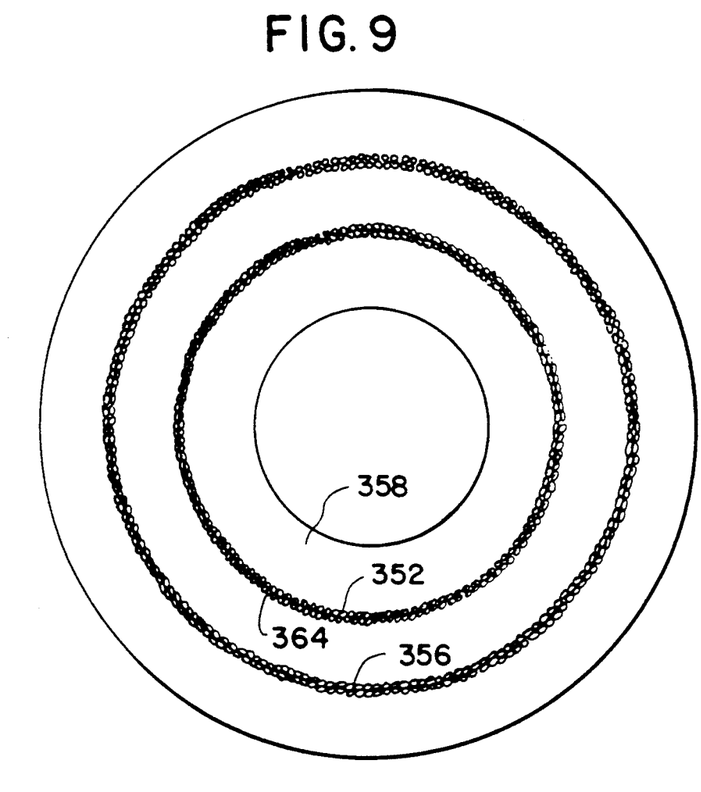
FIG. 9 is a top view of one embodiment of the types of regions within the substantially continuous density gradient solution which may be generated during rotation of the centrifuge of FIG. 3.

As the separation of the pancreatic digest is initiated by centrifugation, substantially annular, regions having constituents of a particular density or range of densities begin to form as illustrated in FIG. 9. For purposes of simplicity of illustration, only two of such regions are represented, each of which contains a particular type of constituent of a given density or range of densities. Moreover, it should be appreciated that there may be a given distribution of densities across each of the regions such that the regions may not be sharply defined. Consequently, in practice the regions may be wider (e.g., a larger radial extent) and encompass a range of densities of constituents. Therefore, under some circumstances only a portion of a given region will be collected and used.

In the example of FIG. 9, the first region 352 is the innermost of two regions and contains the desired islets, whereas the second region 356 is the outermost of the two regions and contains exocrine tissues, which typically have a greater density than that of the islets. In order to remove the islets of the first region 352 from the processing bag 136, hydraulic fluid 290 (FIG. 3) is provided to the lower chamber 120 (FIG. 3) of the centrifuge 72 (FIG. 3) to first force an inner portion 358 from the processing bag 136 which contains that portion of the substantially continuous density gradient solution having a density less than that of the islets within the first region 352. The inner portion 358 is forced through the tubing harness 172 (FIG. 3) and into an appropriate one of the collection containers 300, 304, 308 (FIG. 3). Thereafter, the first region 352 of the desired islets may be collected in a similar manner and directed to another one of the collection containers interconnected with the tubing harness 172 (FIG. 3). In actuality, there may be a number of regions of islets which may each be collected in the described manner.

As can be appreciated, it may be desirable in some circumstances to obtain islets of a particular density in a certain degree of purity. In this case, the region containing such islets should not extend into portions of the gradient solution having a lesser density than the density of the islets so as to not decrease the purity of the harvested islets. Consequently, in order to maximize the amount of the pancreatic digest which may be loaded onto a gradient solution to achieve the desired degree of islet purity, it is desirable to position the islets at a region within the substantially continuous density gradient solution so that at least one of the regions of islets has a maximum vertical surface area for the boundary between the region 352 and the adjacent portion of the gradient solution, considering however the effects of the centrifuge rim 92 on the islets. More particularly, it may be desirable to maximize the boundary area 364 between the given region 352 of islets and the adjacent portion of the gradient solution having a greater density since the height of the processing bag 136 varies as illustrated in FIGS. 5A-5D. In this regard, due to the profile of the processing bag 136, it is nonetheless desirable for the islets to be positioned within "deeper" portions of the processing bag since it may further maximize the amount or purity of islets which may be collected.

Figure 10:
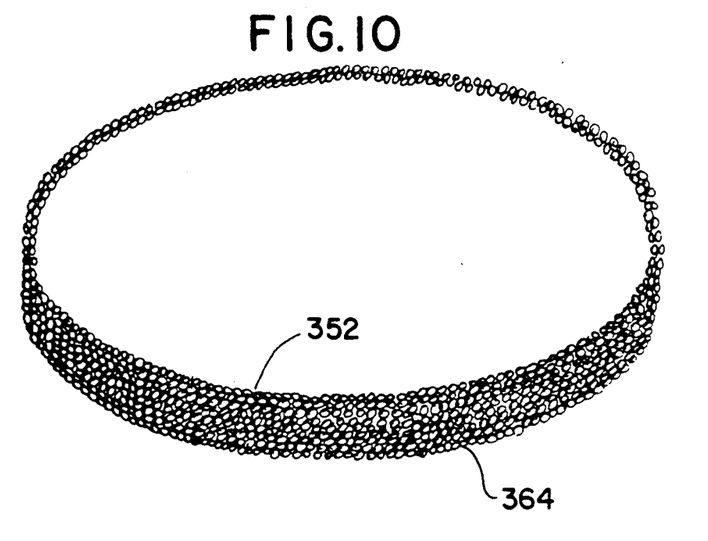
FIG. 10 is a perspective view illustrating the boundary area of one of the regions of FIG. 9.

Based upon the configuration of the centrifuge bowl 76 as illustrated in FIG. 3, which has a radius of approximately 11.3 cm measured from its rotational axis A to the upper portion of the rim 92, it may be preferable for the islets to collect at a region within the substantially continuous density gradient at a radial position from the axis A ranging from about 9.0 to about 9.5 cm. In this region of the centrifuge bowl 76, the bowl 76 has a height of about 2.5 cm such that the vertical surface area of the boundary 364 of this region, illustrated in FIG. 10, is about 694 cm$^2$. Consequently, it can be appreciated that the surface area of this boundary 364 of the region 352 may be maximized without undesirably increasing the overall size of the centrifuge 72. Notwithstanding the foregoing, it should again be appreciated that each region of islets may in fact be comprised of a certain distribution of densities. Therefore, the ability to collect islets of only a particular density may be difficult in practice to achieve.

In order to further illustrate the above-described principles of the present invention, the following example is provided regarding the collecting of islets of Langerhans in the above-described centrifuge 72. Notwithstanding the presentation of this example, those skilled in the art will appreciate that the principles of the present invention may be applied to a plurality of applications, and therefore the present invention is not limited by the following:

Example

Referring to FIG. 3, the processing bag 136 is positioned within the centrifuge bowl 76 and interconnected with the tubing harness 172 in the above-described manner. Prior to providing the substantially continuous gradient solution to the processing bag 136, rotation of the centrifuge bowl 76 is initiated. When rotating at an appropriate velocity, such as approximately 3,000 RPM, 150 milliliters of a solution having a density of 1.10 g/cm$^3$ is provided to the processing bag 136 from the first container 328 (FIG. 6) of the gradient maker 324 (FIG. 6). Thereafter, the valve 336 (FIG. 6) between the first and second containers 328, 332 (FIG. 6) of the gradient maker 324 (FIG. 6) is opened to initiate the formation of the substantially continuous density gradient. In this regard, the substantially continuous gradient solution provided to the processing bag 136 is 300 milliliters and ranges from 1.075 g/cm$^3$ to 1.10 g/cm$^3$. The islets are thereafter loaded into the processing bag 136 via the tubing harness 172 in 100 milliliters of a solution having a density of 1.0 g/cm$^3$. The pancreatic digest having such islets therein may be within the first container 296. In order to remove any islets which have collected on the inner walls of the portion of the tubing harness 172 through which the islets passed, an additional 50 milliliters of the 1.0 g/cm$^3$ solution is provided to the processing bag 136.

When the islets have been loaded onto the gradient and with the centrifuge bowl 76 rotating at a velocity of about 2400 RPM for a time period of about 5 minutes, the islets will migrate to the portion of the gradient coinciding with their particular density. In this regard, the islets typically have a density of about 1.075 g/cm$^3$ and the exocrine which is present in the pancreatic digest concentrate typically has a density of about 1.080 g/cm$^3$. When appropriate separation has been achieved, hydraulic fluid 290 is provided to the lower chamber 120 of the centrifuge bowl 76 such that fractions are removed from the processing bag 136 in an inward to outward manner. When the fraction containing the separated islets therein is evident in the tubing harness 172, such may be directed to an appropriate collector such as the second container 300.

A number of methods may be utilized to gauge the harvesting of the islet fraction(s). For instance, a volumetric basis may be utilized. More particularly, a first fraction of 100 ml. may be removed from the processing bag 136 which coincides with the 1.0 g/cm$^3$ solution and such may be provided to the third container 304. Subsequent fractions of 50 ml. of the solution may be provided to additional containers 300 or 308. The remainder within the processing bag 136 may thereafter be appropriately deposited upon removal of the processing bag 136 from the centrifuge bowl 136. In the foregoing, the particular volumes are removed from the processing bag by providing hydraulic fluid to the lower chamber 120 at a flow rate of 100 ml./min.

As an alternative to the foregoing, the islet fraction(s) may be harvested by visual observation of such fraction(s) rising within the tubing harness 172. In this case, when such fraction(s) reaches an appropriate position within the harness 172, the valves 312 may be manipulated to direct such islets to the appropriate collector. Moreover, sensors 316 may be incorporated in the tubing harness 172 to detect the presence of such islet fraction(s). Furthermore, removal may be based upon predetermined time intervals utilizing a fixed flow rate for the hydraulic fluid 290.

The foregoing description of the invention has been presented for purposes of illustration and description. Further, the description is not intended to limit the invention to the form disclosed herein. Consequently, variations and modifications commensurate with the above teachings, and the skill and knowledge of the relevant art, are within the scope of the present invention. The explain best modes known of practicing the invention and to enable others skilled in the art to utilize the invention in such, or other, embodiments and with the various modifications required by the particular applications or uses of the invention. It is intended that the appended claims be construed to include alternative embodiments to the extent permitted by the prior art.

What is claimed is:

1. A method for separating a plurality of at least one type of an microscopic unit from an microscopic unit-containing fluid, comprising the steps of:
    providing a centrifuge;
    positioning a processing container in said centrifuge;
    rotating said centrifuge and said processing container;
    providing a substantially continuous density gradient solution to said processing container;

providing said microscopic unit-containing fluid to said processing container;

separating said plurality of microscopic units from remaining portions of said microscopic unit-containing fluid based upon a density of said microscopic units within said substantially continuous density gradient solution; and harvesting said plurality of separated microscopic units from said processing container during at least a portion of said rotating step.

2. A method, as claimed in claim 1, wherein:
said providing said substantially continuous density gradient solution step is performed during at least a portion of said rotating step.

3. A method, as claimed in claim 1, wherein:
said substantially continuous density gradient solution extends radially within said processing container relative to said rotational axis.

4. A method, as claimed in claim 3, further comprising:
maintaining said radial extent of said substantially continuous density gradient during said harvesting step.

5. A method, as claimed in claim 1, wherein:
said providing said microscopic unit-containing fluid step is performed after said providing a substantially continuous density gradient solution step.

6. A method, as claimed in claim 1, wherein:
said providing said microscopic unit-containing fluid step is performed before said providing a substantially continuous density gradient solution step.

7. A method, as claimed in claim 1, wherein:
said separating step comprises creating a plurality of regions, each said region being defined by at least one density, said regions collectively extending from a first position within said processing container to a second position within said processing container radially outward from said first position, said plurality of separated microscopic units being contained within at least one of said regions.

8. A method, as claimed in claim 7, wherein:
said harvesting step comprising sequentially removing said regions from said processing container in an order of increasing density.

9. A method, as claimed in claim 1, wherein:
said microscopic units are islets of Langerhans.

10. A method for using a centrifuge for separating a plurality of at least one type of a microscopic unit having a density from a microscopic unit-containing fluid, said centrifuge having a container that is centrifugally rotated by the centrifuge and being adapted to feed fluids into the container while the container is rotating and being further adapted to remove fluids from the container while the container is rotating, comprising the steps of:

centrifugally rotating the container;

creating a continuous density gradient fluid having a maximum density that is not less than the density of the microscopic unit and a minimum density that is not more than the density of the microscopic unit and further having a substantially continuous range of densities between the maximum density and the minimum density;

feeding the continuous density gradient fluid into the container while the container is rotating with the density of the fluid being fed gradually decreasing from the maximum density of the continuous density gradient fluid to the minimum density of the continuous density gradient fluid;

feeding the microscopic unit containing fluid into the container while the container is rotating;

continuing to centrifugally rotate the container to concentrate the microscopic units in a fraction of the continuous density gradient fluid that has a density similar to the density of the microscopic units; and removing from the container while the container is rotating the fraction of the continuous density gradient fluid having a density that is similar to the density of the microscopic units and concurrently removing the concentrated microscopic units from the container.

11. A method as defined in claim 10 wherein the step of feeding the continuous density gradient fluid is performed before the step of feeding the microscopic unit containing fluid.

12. A method as defined in claim 10 wherein the step of feeding the microscopic unit containing fluid is performed before the step of feeding the continuous density gradient fluid.

13. A method as defined in claim 10 further comprising the step of:
removing from the container while the container is rotating a fraction of the continuous density gradient fluid having a density less than the density of the microscopic units.

14. A method as defined in claim 10 further comprising the step of:
removing from the container while the container is rotating a fraction of the continuous density gradient fluid having a density greater than the density of the microscopic units.

15. A method as defined in claim 10 wherein:
the density of each one of the plurality of microscopic units is less than a higher microscopic unit density and more than a lower microscopic unit density; and the fraction of the continuous density gradient fluid has a substantially continuous density from approximately the lower microscopic unit density to approximately the higher microscopic unit density.

16. A method, as claimed in claim 10, wherein:
said microscopic units are islets of Langerhans.

* * * * *